United States Patent

Eklund et al.

[11] Patent Number: 6,055,666
[45] Date of Patent: May 2, 2000

[54] FACE SHIELD

[76] Inventors: Jörgen Eklund, Ydregatan 16, S-582 47 Linköping; Kjell Mases, Knuthsvägen 4, S-780 41 Gagnef, both of Sweden

[21] Appl. No.: 08/930,553
[22] PCT Filed: May 14, 1996
[86] PCT No.: PCT/SE96/00625
   § 371 Date: Oct. 2, 1997
   § 102(e) Date: Oct. 2, 1997
[87] PCT Pub. No.: WO96/36303
   PCT Pub. Date: Nov. 21, 1996

[30]    Foreign Application Priority Data

May 19, 1995 [SE] Sweden ................................ 9501885-9

[51] Int. Cl.⁷ ........................... A41D 13/00; A61F 9/06
[52] U.S. Cl. .................................................. 2/9; 2/8
[58] Field of Search ...................... 2/8, 9, 424, 10; 128/206.21, 206.28

[56]    References Cited

U.S. PATENT DOCUMENTS

| | | |
|---|---|---|
| 2,377,122 | 5/1945 | Bakke . |
| 2,388,604 | 11/1945 | Eisenbud ........................................ 2/8 |
| 3,232,290 | 2/1966 | Nicolai . |
| 3,438,060 | 4/1969 | Lobelle et al. . |
| 3,838,466 | 10/1974 | Poirier ........................................... 2/10 |
| 3,868,726 | 3/1975 | La Marre et al. ............................. 2/8 |
| 4,101,979 | 7/1978 | Tarrone ........................................... 2/8 |
| 4,514,864 | 5/1985 | Huber ........................................... 2/424 |
| 4,704,746 | 11/1987 | Nava . |
| 5,029,342 | 7/1991 | Stein et al. . |
| 5,031,237 | 7/1991 | Honrud . |

FOREIGN PATENT DOCUMENTS

| | | |
|---|---|---|
| 1124100 | 10/1956 | France . |
| 2335200 | 7/1977 | France . |
| 2611489 | 9/1988 | France . |
| 1 041 802 | 10/1958 | Germany . |
| 32 33 467 | 3/1985 | Germany . |
| 473592 | 7/1969 | Sweden . |
| 1 569 088 | 6/1980 | United Kingdom . |

*Primary Examiner*—Micheal A. Neas
*Attorney, Agent, or Firm*—Young & Thompson

[57]    ABSTRACT

A face shield to be placed in front of the face of a wearer includes at least one light transparent part and a holding device for holding on to the face shield, the face shield includes at least one air deflecting device which is arranged, with the help of the directional effect and kinetic energy of the exhalation air to lead away the exhalation air from the region where the nose and mouth of the wearer are to be positioned, and that the inhalation air is supplied to the region where the nose and mouth of the wearer are to be positioned in essentially different directions to those in which the exhalation air is led away, so that a separation of the inhalation air and exhalation air is achieved.

12 Claims, 3 Drawing Sheets

FACE SHIELD

BACKGROUND OF THE INVENTION

The invention relates to a face shield intended to be placed before the face of a wearer, components for such a face shield and a method for reducing the mixing of exhalation air in the inhalation air in such a face shield.

DESCRIPTION OF THE RELATED ART

During work such as welding and mechanical processing, face shields are required in order to prevent the eyes and face being subjected to ultraviolett light, heat, toxic substances, particles or other factors which can cause damage to these body parts.

For a long time it has been a problem in work where face shields are used that the wearer often suffers from fatigue, headaches and dizziness. The causes of this have been shown to be, amongst others, an increased carbon dioxide content in the inhalation air of the wearer when face shields are used. Experiments have shown that the inhalation air behind a face shield has an increased carbon dioxide content because of the mixing in of exhalation air. There are both limits and recommendations for the permitted content of carbon dioxide in inhalation air.

Mechanical measures for blowing away welding smoke from in front of a welding screen through sucking air from the inside of the welding screen and in this way producing an increased air circulation in front of the welding screen, have been taken in the American Patent U.S. Pat. No. 5,029,342, which shows a welding screen comprising a fan which is driven by solar cells. The fan sucks air from the inside of the welding screen and out through the front surface of the welding screen in a direction towards the welding place with the intention of preventing smoke from reaching the welding screen. The disadvantages of this construction are that, in order to achieve an effective blowing effect, a relatively large amount of air is required which causes draughts inside the welding mask and that the airflow through the fan is regulated by the welding light and not according to the ventilation requirements that the wearer has.

The prior art also includes the American Patent U.S. Pat. No. 2,377,122, in which a welding helmet is shown in the form of a separable cover, which is placed over the head and shoulders of the wearer. A breathing mask covers the nose and mouth, whereby inhalation air is led from air intakes at the upper back part of the welding helmet to the mask via two hoses. There is a non-return valve by each of the air intakes, which opens so that air can be sucked in through the hoses. Exhalation air is led out from the breathing mask through a non-return valve in the face mask and out through the front surface of the welding helmet via a nozzle. The disadvantages in this construction are the large breathing resistance which the inhalation air meets through the hoses, which means that it becomes strenuous for the wearer to breathe, and that a volume of exhalation air is supplied to the breathing mask during exhalation where-by the carbon dioxide content increases in the inhalation air in the subsequent inhalation. Further disadvantages are moisture problems, the risk of allergies and the feeling of discomfort which the wearer can experience when a breathing mask is placed over the nose and mouth for a long time.

A problem with high head temperatures and fogging of the visor occurs in integral helmets for use in e.g. motor-cycling or the like. Owing to this there is a suggestion in U.S. Pat. No. 4,704,746 to ventilate an integral helmet with the help of the relative wind which occurs during travel on e.g. a motorcycle. A front channel communicates on the one hand with the inside of the helmet via openings, on the other hand with the outside of the helmet via an opening which is provided with an adjustable valve. In a first ventilation position, air is supplied to the helmet from the outside of the helmet via the front channel. In a second ventilation position, the valve is struck by the relative wind, whereby an underpressure occurs in the front channel. Consequently, air is sucked out from the inside of the helmet through the front channel. On the topside of the helmet there is a further opening which has connection with the inside of the helmet. Because of the relative wind an underpressure occurs by the opening, whereby air is sucked from the inside of the helmet. Air is supplied to the helmet by the relative wind via the openings in the frontside, whereby the air which is supplied passes on the inside of visor in order to prevent fogging. Consequently, an effort is made to solve the ventilation problem of integral helmets with the help of the under and overpressures which form in the ventilation channels because of the relative wind.

SUMMARY OF THE INVENTION

The main object of the present invention is to produce a face shield which without mechanical ventilation and without the supply of external energy holds the inhalation air free from the exhalation air and thereby permits a lower carbon dioxide content in the inhalation air.

A further object of the present invention is to produce a face shield which avoids the above mentioned disadvantages in known face shields.

Yet another object of the present invention is to reduce the moisture content behind a face shield in order to prevent fogging and furthermore reduce the physiological stress.

Further objects of the present invention are to lower the temperature behind a face shield in order to thereby reduce the physiological stress.

In contrast to the prior art, air is removed resp. supplied to the face cover according to the present invention through the kinetic energy and directional effect of the exhalation air resp, the underpressure which the inhalation air produces.

In accordance with the invention, the problem of a too high content of carbon dioxide in the inhalation air is solved with a surprisingly small consumption of resources through the use of the fact that the exhalation air, because of physiological and physical reasons, has a greater speed and range than the inhalation air.

By placing air deflecting means, possibly comprising channels, in and from the region for exhalation air during exhalation and at a sufficient distance from the nose and mouth, the exhalation air can be effectively led away, in particular, rearwardly. The exhalation air can then be let out at places by the edges of the face shield or through openings in its surface, while inhalation air, because of its lower speed and for physical reasons, can be sucked in diffusely from directions with a low flow resistance, which in particular occurs from the volume along the face.

BRIEF DESCRIPTION OF THE DRAWINGS

The invention will now be described more closely in the form of embodiments with reference to the appended drawings.

DESCRIPTION OF THE PREFERRED EMBODIMENTS

Figure 1:
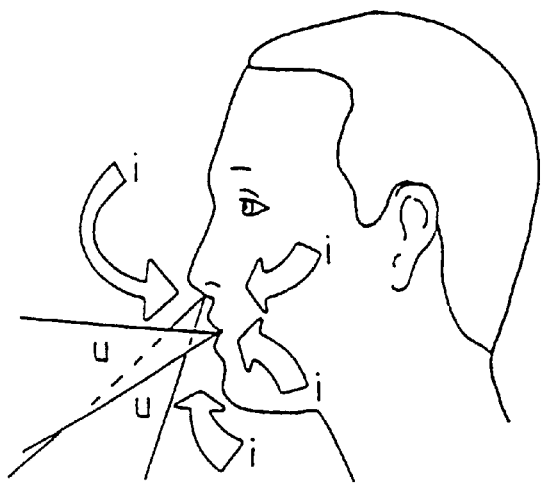
FIG. 1 depicts the different directions of inhalation resp. exhalation air for a person seen in profile.

FIG. 1 shows the different inhalation and exhalation air directions on a person seen in profile. The exhalation air from the nose usually occurs in a direction diagonally downwards and the exhalation direction from the mouth usually occurs forwardly. These exhalations directions are different for different people. Because the exhalation air has a higher speed and range than inhalation air, air flows are formed in front of the face which cause a large part of the air which is inhaled to come in towards the mouth and nose along the surface of the face, as shown with arrows in FIG. 1.

Figure 2:
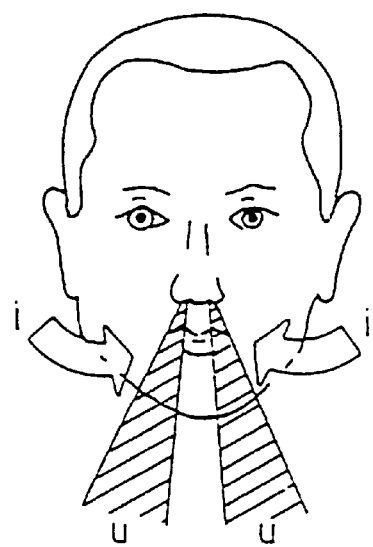
FIG. 2 depicts the directions of inhalation and exhalation air for the nose of a person seen from the front.

FIG. 2 shows the different directions of inhalation and exhalation air on a person seen from the front. The exhalation air from the nose is normally divided into two different directions which vary from person to person.

When a face shield of the prior art is placed in front of a face, a large amount of the exhalation air will remain behind the shield when the next inhalation takes place, which leads to the exhalation being mixed with the inhalation air, whereby the carbon dioxide content in the inhalation air increases. By providing one or more air deflecting means on the inside of the face shield in accordance with the invention, the exhalation air can be led away from the region where the nose and mouth of the wearer are positioned so that the content of exhalation air in the next inhalation is reduced.

Figure 3:
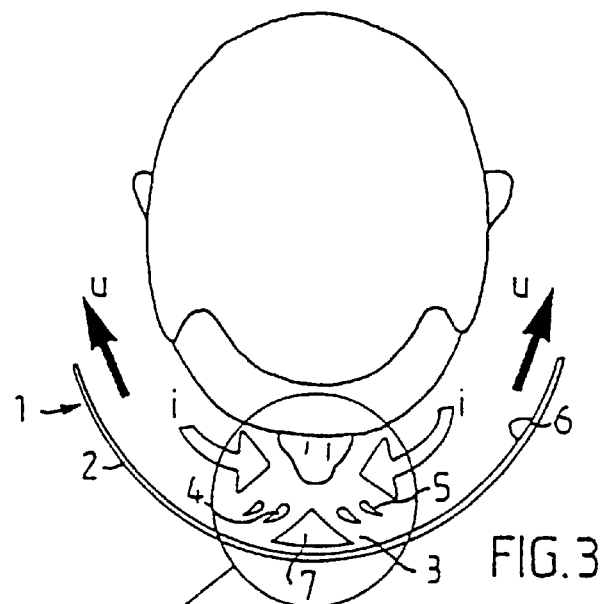
FIG. 3 is a schematic view from above of a face shield with air deflecting means according to a first embodiment.
Figure 4:
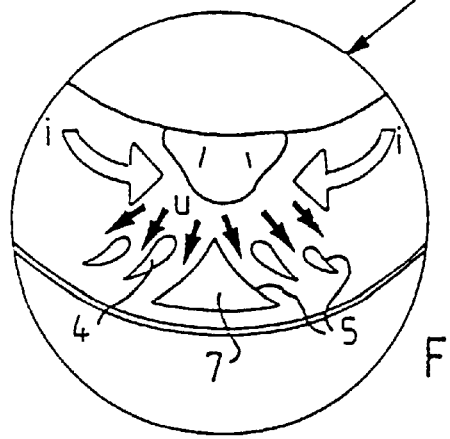
FIG. 4 concerns a partial magnification of FIG. 3.

In a first embodiment according to FIG. 3, a face shield 1 is shown schematically which comprises an outer wall 2, which is provided with air deflecting means 3 in order to lead away exhalation air u. The air deflecting means 3 in this example is formed from guiding profiles 4 which form deflecting surfaces 5 for the exhalation air. The guiding profiles 4 can be placed at a distance from the outer wall 2, as is shown in FIG. 4, or provided directly on the inner surface 6 of the outer wall 2. The outer wall 2 can also be formed so that the guiding profiles form an integral part of the outer wall 2, whereby the guiding profiles 4 and the outer wall 2 are manufactured in one piece. The guiding profiles 4 can be arranged substantially symmetrically on both sides of a separation edge 7 which faces towards the place where the face of the wearer is intended to be positioned. Deflecting surfaces 5 for exhalation air extend out on both sides of the separation edge 7, whereby these deflecting surfaces 5 can be substantially concave arched. The separation edge 7 can also be single-sided and direct exhalation air towards one side.

Figure 5:
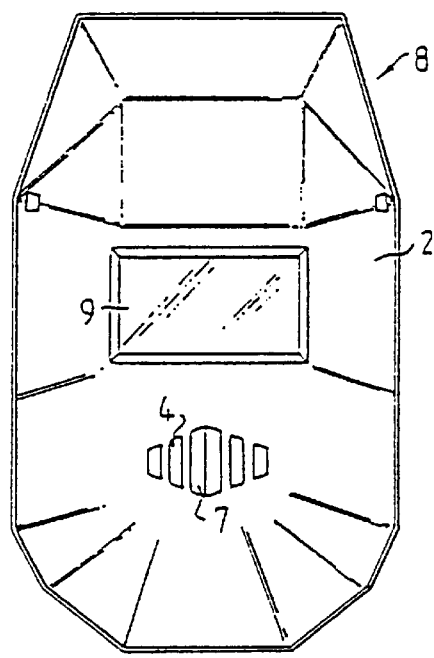
FIG. 5 shows a welding screen according to FIG. 3 with the air deflecting means, seen from the back.

FIG. 5 shows how the guiding profiles 4 and the separation edge 7 according to the first embodiment are placed on the inside of a welding screen 8. In the region where the eves of the wearer are intended to be positioned, a light transparent part 9 in the form of a view opening with a protective glass is arranged. The protective glass can, for example, be formed of a partially light transparent material such as an IR- and/or UV-filter, or a so-called fast filter, i.e. a light filter which is quite light until affected by welding light, whereby the filter becomes dark.

Figure 6:
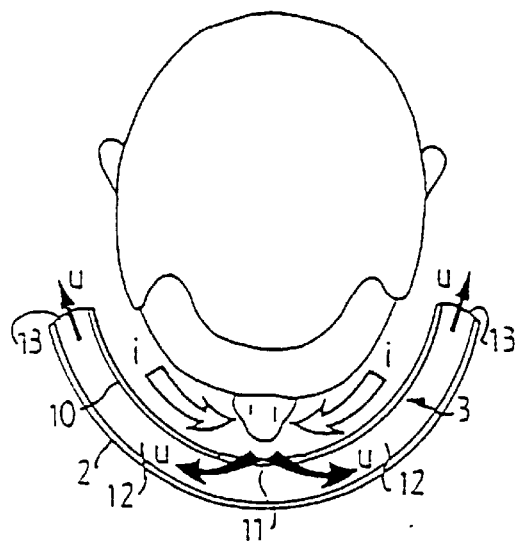
FIG. 6 is a schematic view from above of a face shield with air deflecting means according to a second embodiment.

In a second embodiment according to FIG. 6, the air deflecting means 3 are formed by an inner wall 10 which is connected with the inside of the outer wall 2. The inner wall 10 shall be placed at a sufficient distance from the nose and mouth of the wearer. Exhalation air u passes through an opening 11 in the inner wall 10, can divide up and flow in one or more evacuation channels 12 which are formed between the outer and inner wall 2 resp. 10, and thereafter leave the evacuation channels 12 through the outlet openings 13. Because the kinetic energy and directional effect of the exhalation air u are greater than that of the inhalation air i and because of the inertia in the airflow which the exhalation air causes in the evacuation channels 12, the exhalation air u carries with it a part of the pure air between the face and the face shield. whereby exhalation air u from the evacuation channel 12 will be minimized in the subsequent inhalation. The inhalation air i will to a high degree be supplied to the mouth and nose through the space which is formed between the inner wall 10 and the face, and the space which is formed between the outer wall 2 and the face. The opening 11 shall have a limited size and can be optimized for the different directions which exhalation air has. The opening 11 can be designed to fit the anthropometry of most people.

Figure 7:
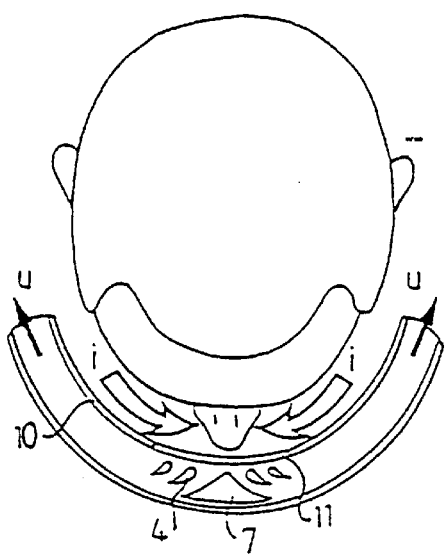
FIG. 7 is a schematic view from above of a face shield with air deflecting means according to a third embodiment.

In order to further reinforce the separation of the inhalation and exhalation air in a face shield, the air deflecting means 3 according to the embodiment above can be combined according to a third embodiment, as shown in FIG. 7. By attaching the guiding profile 4 and separation edge 7 between the opening 11 in the inner wall 10 and the outer wall, the formation of vortexes in, and rebounding of, the exhalation air u is prevented so that it is not mixed with the inhalation air i. This third embodiment helps also to increase the flexibility of the face shield so that it can be used by everybody, for example with different breathing angles.

Figure 8:
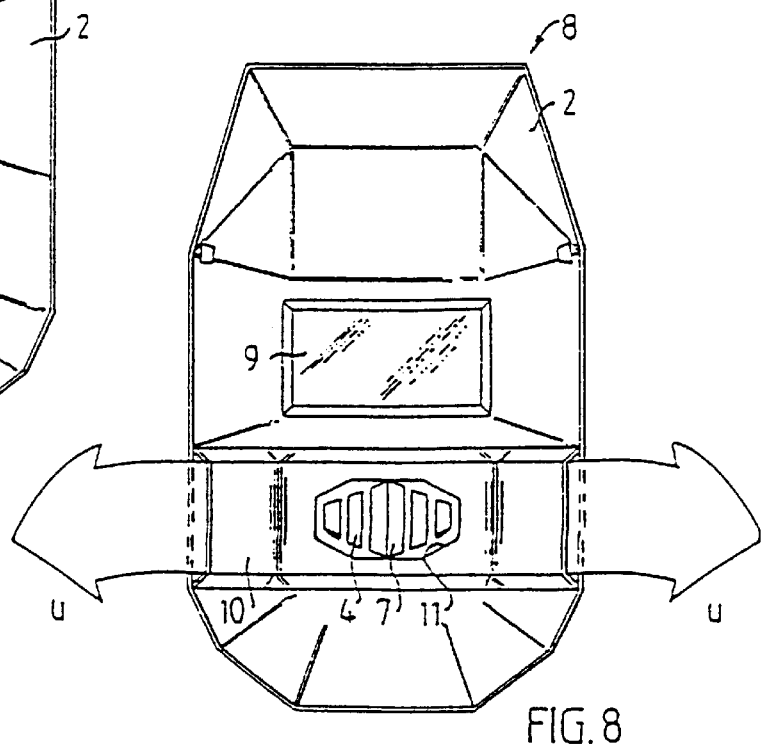
FIG. 8 shows a welding screen according to FIG. 7 with air deflecting means seen from the back.

FIG. 8 shows how the air deflecting means according to the third embodiment are placed on the inside of a welding screen 8. In the region where the eves of the wearer are intended to be placed, a light transparent part 9 is arranged in the form of a view opening with a protective glass. The protective glass can, for example, be made of a partially light transparent material, such as an IR- and/or UV-filter, or a so-called fast filter.

Figure 9:
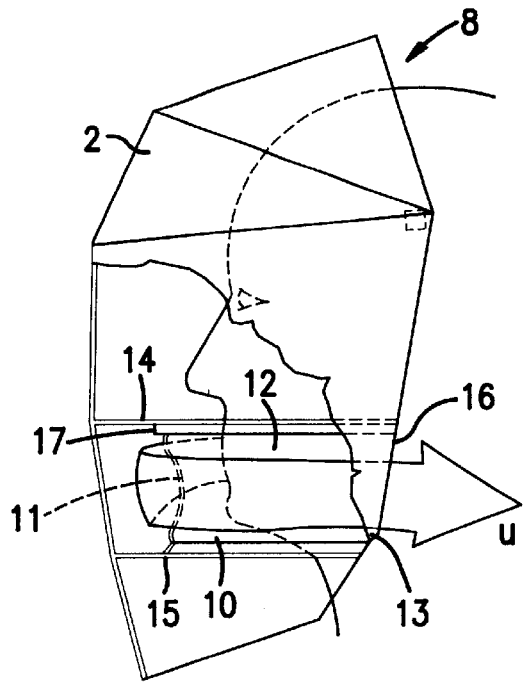
FIG. 9 is a perspective view of a face shield, according to the second embodiment, placed on a wearer.

FIG. 9 shows a perspective view of a face shield in the form of a welding screen 8 according to the second embodiment above. The outer wall 2 in FIG. 9 is partially cut away in order to show how the inner wall 10 is arranged on the inside of the outer wall 2. The outer wall 2 supports a light transparent part 9, e.g. a light filter (not shown), which makes it possible for the wearer to see through the outer wall 2. The upper edge 14 resp. the lower edge 15 of the inner wall 10 are closely joined with the outer wall 2, for example through the upper edge 14 resp. the lower edge 15 being bent outwards in a direction away from the wearer and fastened to the outer wall 2, so that evacuation channels 12 between the inner and outer walls 2 resp. 10 are formed. The side edges 16 of the inner wall 10 delimit together with the outer wall 2 a passage so that an outlet opening 13 is formed between the outer and inner walls 2 resp. 10 on both sides of the outer wall 2.

There is an opening 11 in the inner wall 10 through which the exhalation air u flows. The opening 11 is suitably placed and shaped in such a way that the exhalation air u from the nose and mouth, without being hindered by the inner wall 10, can pass through the opening 11 and further through the evacuation channels 12 and out through the outlet orifices 13. The opening 11 should be shaped optimally so that a plurality of different people should be able to use the same model of welding screen 8. It is important that the opening 11 is formed at a distance from the upper edge 14 of the inner wall 10 so that a part 17 of the inner wall 10 remains between the upper edge 14 of the inner wall 10 and the upper edge of the opening 11. This part 17 can, however, be arranged around the opening 11 and contributes to preventing exhalation air u from rebounding back towards the face of the wearer.

The outer and inner walls 2 resp. 10 are preferably bent in order to also protect the face and head from the side. It is, however, possible to form the outer and inner walls 2 resp. 10 with flat surfaces which are angled so that a front side and side surfaces are formed. Preferably, the outer wall 2 extends over the forehead and a part of the top of the head as well as downwardly over the chin and the throat. The outer wall 2 can however, be shaped so that only the region around the mouth, nose and eyes are covered. Furthermore, the distance between the inner wall 10 and the face should be sufficiently large to allow room for the inhalation air along the surface of the face.

Figure 10:
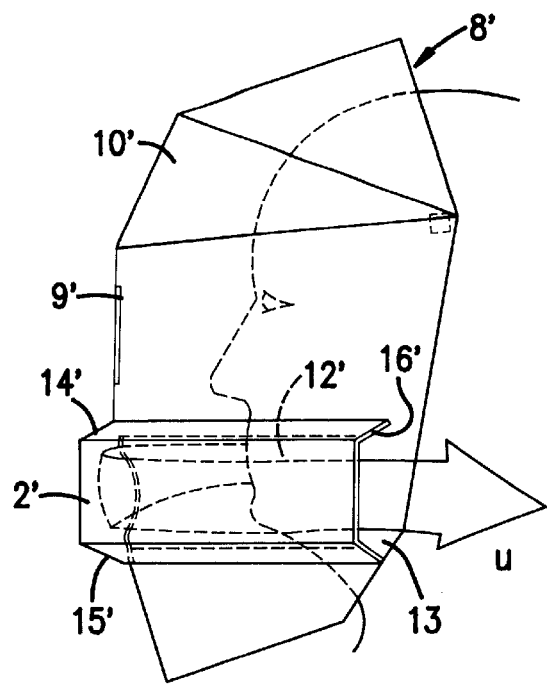
FIG. 10 is a perspective view of a face shield, according to a fourth embodiment, placed on a wearer.

FIG. 10 shows a fourth embodiment of a face shield in the form of a welding screen 8'. In this embodiment the air deflecting means 3 is formed by the outer wall 2' which is placed on the outside of the inner wall 10'. The inner wall 10' has a light transparent part 9', for example a view opening with a protective glass (not shown). The upper edge 14' resp. the lower edge 15' of the outer wall 2' are tightly connected with the inner wall 10', for example by the upper edge 14' resp, the lower edge 15' being bent inwardly in the direction towards the wearer and fastened to the inner wall 10' so that the evacuation channels 12' are formed between the outer and inner walls 2' resp. 10'. The side edges 16' of the outer wall 2' do not, however, lie against the inner wall 10', whereby an outlet orifice 13' is formed between the outer and inner walls 2' resp. 10' on both sides of the inner wall 10'.

Figure 11A:
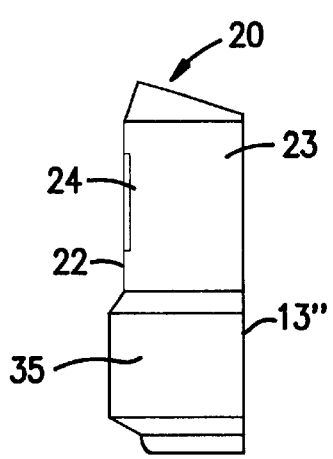
FIGS. 11 and 11A are sideviews of a face shield and a cover therefor, according to a fifth embodiment.
Figure 11:
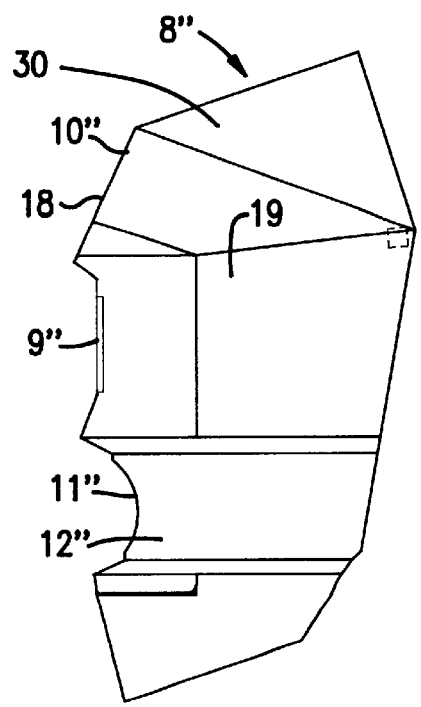

According to a fifth embodiment shown in FIGS. 11 and 11A, a welding screen 8" can be formed as an integrated unit with an air deflecting means 3 in the form of a cover 20 (FIG. 11A) acting as an outer wall, which in cooperation with an inner wall 10" forms evacuation channels 12". The inner wall 10" comprises a front side 18 and side walls 19. By bending a part of the side walls 19 of the inner wall 10" inwardly in the direction towards the wearer and moving a part of the front side of the inner wall 10" inwardly in the direction towards the wearer, these surfaces form a wall surface which is placed nearer to the face of the wearer than the other surfaces of the inner wall 10". In the inwardly displaced front side 18, in the region around the mouth and the nose, an opening 11" is made through which the exhalation air u can flow. In the inwardly displaced front side 18, in the region where the eyes of the wearer are intended to be positioned, a light transparent part 9" in the form of a view opening with a protective glass is arranged. The protective glass can, for example, be formed from a partially light transparent material, such as an IR- and/or UV-filter, or a so-called fast filter.

On the outside of the front side of the inner wall 10", the cover 20 is applied over the parts which are inwardly displaced. The cover 20 is arranged to close tightly around the inner wall 10", except at a part of the sides of the inner wall 10" at which the outlet orifices 13" for the exhalation air u is formed. The evacuation channels 12" through which the exhalation air u can flow are thereby formed between the cover 20 and the parts which are inwardly displaced or bent. The evacuation channels 12" exit on each side of the welding screen 8" at the outlet orifices 13". The inhalation air i passes between the inner wall 10" and the face. The cover 20 is equipped with a front surface 22 and side surfaces 23 attached to this front surface 22. The cover 20 is equipped with a light transparent part 24 and equipped with an arrangement for easily attaching it to and removing it from the inner wall 10" with the intention of facilitating cleaning and changing of the protective glass.

The welding screen 8,8',8" can be arranged on the head of the wearer by holding means such as known yokes, frames or supports (not shown) which are attached to the welding screen 8,8',8" and arranged over the head. Other types of arrangements for placing the welding screen 8,8',8" in front of the face of the wearer are also conceivable. It is, however, important that the welding screen 8,8',8" is placed at distance from the face of the wearer so that a column or a space is formed between the face and the wall arranged nearest to the face, i.e. the inner wall 10,10',10". This permits the inhalation air i to pass between the face and the inner wall 10,10',10". At the same time the uncomfortable feeling which can occur when an object is placed closely over the face is avoided.

Heat is given off during welding whereby the welding screen 8,8',8" used by the welder becomes heated up, which means that the temperature inside the welding screen 8,8',8" increases. By arranging a reflective layer 30 on the front surface of the welding screen 8,8',8", the heating up can be minimized. In order to increase the flow of the exhalation air u in the evacuation channels 12,12',12" and its ability to leave the outlet orifices 13,13',13", a part of the outer side of the welding screen 8, 8',8" can be coated with a heat absorbent layer, layer 35, e.g. black paint, in the region around the outlet orifices 13,13',13" in order to achieve convection and thermals close to the outer surface of the welding screen 8,8',8".

The evacuation channels and the outlet orifices can be orientated in order to achieve assisted ejection of the exhalation air because of heat radiation or other thermal air movements. In order to increase the flow of the exhalation air from the mouth and nose, the evacuation channels and the outlet orifices can be orientated to take advantage of the thermal forces occurring from the warm exhalation air.

The invention is not limited to the embodiment shown but a plurality of variations are conceivable within the scope of the claims. It is consequently conceivable that the air deflecting means, which form a common feature in the above mentioned embodiments, end at the outlet orifices placed, for example, on the top of, at the bottom of or on the surface of the welding screen. It is also conceivable that the air deflecting means can form a separate unit which can be mounted on an already existing face shield.

In the embodiments shown of the face shield according to the invention, the face shield is symmetrically shaped around an axis of symmetry so that the air evacuation can take place similarly in the two side directions, but it is naturally also conceivable to form the face shield asymmetrically.

The air deflecting means can also be equipped with means, e.g. an one-way valve, which prevents or gives an increased resistance against air flows opposing the direction of the exhalation air. The air deflecting means can also be made adjustable to different positions in the face shield for adapting the face shield to different wearers.

We claim:

1. A face shield, which is intended to be placed in front of the face of a wearer and which comprises:

at least one light transparent part and a holding means intended for holding the face shield, the face shield comprising at least one air deflecting means arranged to lead away exhalation air from a region where the nose and mouth of the wearer are intended to be positioned, and that an inhalation air is supplied to the region where the nose and mouth of the wearer are intended to be positioned from essentially different directions to those in which an exhalation air is removed, so that a separation of inhalation air and exhalation air is achieved, the face shield comprising an inner wall and an outer wall, which are arranged beside one another, so that the inner wall together with the outer wall form at least one evacuation channel, which ends at at least one outlet orifice, that a through opening to the at least one evacuation channel formed in the inner wall is intended to be placed in the region where the nose and mouth of the wearer are intended to be positioned, that the inner wall is intended to be placed at a distance from the face of the wearer, and that the light transparent part is arranged by the inner wall, the inner wall comprising a front side and side walls, wherein the outer wall is formed by a cover which is arrangeable over the front side of the inner wall and the front parts of the side walls, and the cover comprises a light transparent front surface and side surfaces connected thereto, which are connectable to the inner wall.

2. A face shield according to claim 1, wherein the side walls are bent inwardly in the direction towards the place where the face of the wearer is intended to be positioned, from the region where the mouth of the wearer is intended to be positioned to the region where the eyes of the wearer are intended to be positioned, and the front side of the inner wall in the above mentioned region is placed in the direction towards the place where the face of the wearer is intended to be positioned, and connected to the surrounding side walls.

3. A face shield according to claim 1, wherein the light transparent part comprises a view opening with a protective glass, and the outside of the face shield is equipped with a layer which reflects heat radiation except for the regions by the outlet orifices, where instead heat-absorbing layers are arranged in order to obtain convection and thermals.

4. A face shield according to claim 1, wherein a sight opening with a protective glass is arranged in each side surface in which the outlet orifices are placed and directed towards said protective glass.

5. A face shield according to claim 1, wherein the air deflecting means comprises at least one guiding profile, which forms at least one deflecting surface for the exhalation air, whereby the at least one guiding profile is arranged in the region where the exhalation air of the wearer is intended to strike.

6. A face shield according to claim 5, comprising at least two of the at least one guiding profiles which are essentially symmetrically arranged on both sides of a line of symmetry.

7. A face shield according to claim 6, wherein the line of symmetry is formed of a separation edge, which faces towards the place where the face of the wearer is intended to be positioned, and deflecting surfaces for the exhalation air extend from both sides of the separation edge.

8. A face shield according to claim 5, wherein the at least one guiding profile is arranged by the opening.

9. A face shield according to claim 1, wherein the evacuation channels, which are formed between a hood and the inner wall, extend to the sides and one of upwardly and downwardly, and end in outlet orifices arranged on at least one side of a side edge arranged on the face shield.

10. A face shield according to claim 1, wherein the face shield is a welding screen and the light transparent part is formed of one of an IR-filter, a UV-filter, and a fast filter.

11. An inner wall intended to be arranged on a face shield which is intended to be placed in front of the face of a wearer, wherein the inner wall, which forms air deflecting means for exhalation air, is arrangeable on the inside of the face shield, and the inner wall together with an inner surface of the face shield forms at least one evacuation channel, which extends to sides, and one of upwardly and downwardly, and ends in at least one outlet orifice arranged on at least one side edge, and at least one through opening to the formed evacuation channels in the inner wall is intended to be placed in the region where the nose and mouth of the wearer are intended to be positioned, wherein one of a separation edge and at least one guiding profile is arranged between the inner wall and the inside of the face shield in the region for the opening.

12. An outer wall intended to be arranged on a face shield, which is intended to be placed in front of the face of a wearer, wherein the outer wall forming air deflecting means for the exhalation air is arrangeable on an outside of the face shield, and the outer wall together with an outer surface of the face shield forms at least one evacuation channel, which extends to sides, and one of upwardly and downwardly, and ends in outlet orifices arranged on the outside of the face shield, and at least one through opening to the formed evacuation channels in the face shield is intended to be placed in the region where the nose and mouth of the wearer are intended to be positioned, wherein one of a separation edge and at least one guide profile is arranged between the outer wall and the inside of the face shield, in the region for the opening.

* * * * *